US005491122A

United States Patent [19]

Manker et al.

[11] Patent Number: 5,491,122

[45] Date of Patent: Feb. 13, 1996

[54] **FUNGICIDAL AND INSECTICIDAL COMPOUNDS AND COMPOSITIONS DERIVED FROM FUNGAL STRAINS OF *PRENOPHORA TERES***

[75] Inventors: Denise C. Manker, Davis, Calif.; Connie N. Rosendahl, Bromdby, Denmark; Morten Heide, Holte, Denmark; Torben L. Bachmann, Valby, Denmark; Ruby I. Nielsen, Farum, Denmark

[73] Assignees: Novo Nordisk A/S, Bagsvaerd, Denmark; Novo Nordisk Entotech, Inc., Davis, Calif.

[21] Appl. No.: 351,275

[22] PCT Filed: Jun. 18, 1993

[86] PCT No.: PCT/US93/05878

§ 371 Date: Dec. 7, 1994

§ 102(e) Date: Dec. 7, 1994

[87] PCT Pub. No.: WO94/00013

PCT Pub. Date: Jan. 6, 1994

Related U.S. Application Data

[63] Continuation-in-part of Ser. No. 901,369, Jun. 19, 1992, abandoned.

[51] Int. Cl.[6] ........................ A01N 43/36; C07D 207/44; C07D 405/10

[52] U.S. Cl. .................. 504/100; 435/252.1; 435/254.1; 435/255.1; 435/172.1; 514/422; 514/423; 548/517; 548/539

[58] Field of Search ............................. 435/252.1, 254.1, 435/255.1, 172.1; 548/517, 539; 504/100; 514/422, 423

[56] References Cited

U.S. PATENT DOCUMENTS

| | | | |
|---|---|---|---|
| 4,977,275 | 12/1990 | Hasegawa et al. | 548/539 |
| 5,171,740 | 12/1992 | McAlpine et al. | 514/422 |
| 5,244,658 | 9/1993 | Parke | 548/517 |

*Primary Examiner*—Jacqueline Haley
*Attorney, Agent, or Firm*—Steve T. Zelson; Elias J. Lambiris

[57] ABSTRACT

The present invention provides fungicidal and insecticidal active compounds and derivatives thereof, fungicidal and insecticidal compositions comprising said compounds, processes for producing said compounds and the use of said compounds for controlling fungi and/or insects.

18 Claims, No Drawings

FUNGICIDAL AND INSECTICIDAL COMPOUNDS AND COMPOSITIONS DERIVED FROM FUNGAL STRAINS OF *PRENOPHORA TERES*

This application is a National Stage application of PCT/US93/05878, filed Jun. 18, 1993, published Jan. 6, 1994 as WO94/00013, which is a continuation-in-part of U.S. Ser. No. 07/901,369, filed Jun. 12, 1992, now abandoned.

FIELD OF INVENTION

The present invention relates to fungicidal and insecticidal active compounds, compositions and derivatives thereof, and processes for producing such compounds. The invention also relates to fungicidal and insecticidal compositions comprising these compounds, either alone or in combination with other pesticides or growth regulators, and the use of the compounds or compositions of the invention for controlling fungi and/or insects.

BACKGROUND OF THE INVENTION

For a number of years it has been known that various microorganisms produce secondary metabolites exhibiting biological activity so as to be useful as pesticides for controlling diseases and pests.

Although progress has been made in the field of identifying and developing biological pesticides for controlling various diseases and pests in plants and animals of agronomical and horticultural importance, most of the pesticides in use are still synthetic compounds that are difficult to decompose in nature and have a broad spectrum of activity.

In the last decade or so there has been an increasing concern for the impact of such pesticides on the environment and the ecosystems surrounding farmlands, and consequently there exists an outspoken need for pesticides that are more specific in their activity, and are readily degradable in the natural environment.

Natural products provide an alternative to synthetic fungicides and insecticides in that they may have another mode of action, may be more biodegradable and safer in the environment.

Several compounds have been previously isolated from the genus Pyrenophora. The Aspergillomarasamines, including Toxin A (below), are a series of compounds derived from several genera of fungi including Pyrenophora. These compounds are toxic to higher plants and are widely distributed in fungi. (*Physio. Plant Path.*, Vol. 14, pp. 41–46, 1979).

Another series of compounds isolated from a number of genera including Pyrenophora are the Ophiobolins. A report of these phytotoxic and antimicrobial compounds from *P. teres* has not previously been made. (*Proc. Natl. Acad. Sci. USA*, Vol. 84, pp. 3081–3085, 1987). Pyrenolide compounds have been isolated from *P. teres*. (*Agric. Biol. Chem*, Vol. 44, pp. 2761–2762, 1980). However, their biological activity spectrum includes antifungal activity but no insecticidal activity.

Compounds reported from the genus Pyrenophora are the following:

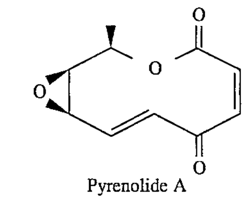

Pyrenolide A

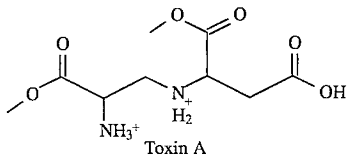

Toxin A

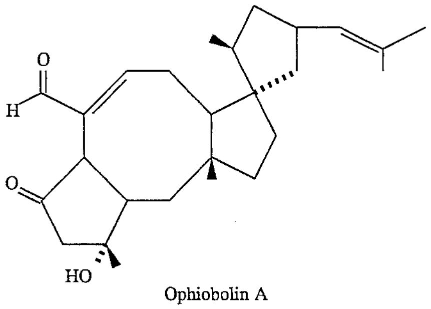

Ophiobolin A

It is, therefore, an object of the present invention to provide novel fungicidal and insecticidal compounds which originate from natural sources or are direct derivatives of such compounds and which confer protection for plants against harmful fungi and insects.

SUMMARY OF THE INVENTION

The present invention is based on the extremely surprising recognition that an extract of the biomass of *Pyrenophora teres* was found to inhibit the growth of fungi, insects and bacteria. Compounds of this structural type have not been previously reported in the literature. Indeed, members of *Pyrenophora teres* have not previously been reported to contain compounds which inhibit the growth of fungi, insects and bacteria.

Generally stated, in one aspect the present invention provides for a substantially pure strain of *Pyrenophora teres* (which belongs to the class Ascomycetes), designated CL806 (International Mycological Institute CC# 35 1438), and a substantially pure fungal strain belonging to the class Deuteromycetes designated 33-971 (International Mycological Institute CC# 355496), and mutants thereof. The invention also relates to the use of these microorganisms to produce the compounds of the invention as fungicidal and/or insecticidal compositions.

More specifically, the invention relates to compounds of formulas I and IV and any tautomers thereof:

I

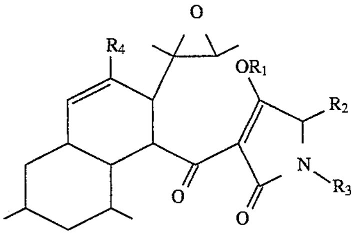

-continued

IV

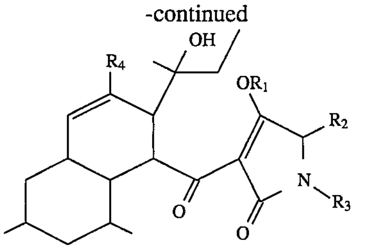

wherein $R_1$ is hydrogen, methyl or acetyl, or $R_1$ is sodium, potassium, lithium or any other salt;

$R_2$ is hydrogen or straight or branched $C_{1-10}$-alkyl;

$R_3$ is hydrogen or straight or branched $C_{1-10}$-alkyl; and $R_4$ is hydrogen or methyl.

$C_{1-10}$-alkyl encompasses methyl, ethyl, propyl, butyl, pentyl, hexyl, heptyl, octyl, nonyl and decyl.

Preferred compounds according to the present invention are the compounds of formulas II, III, V and VI:

II

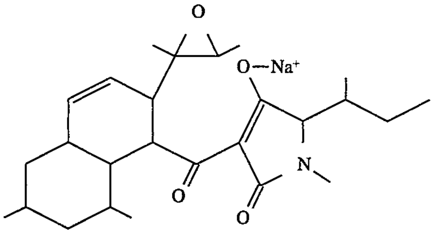

III

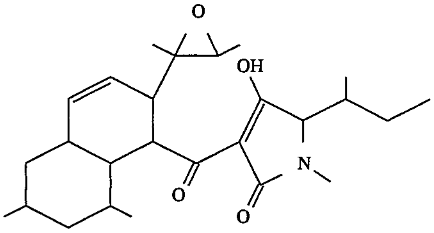

V

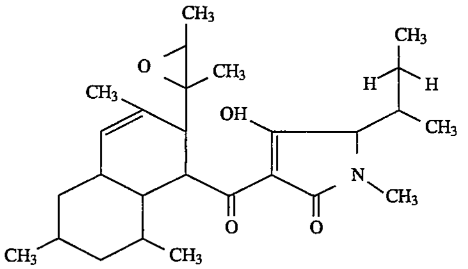

VI

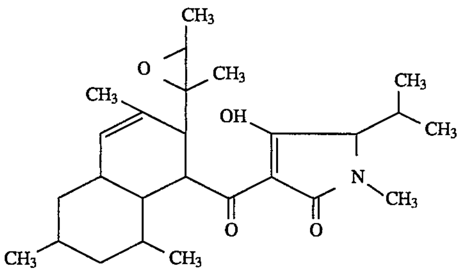

Said compounds and their tautomeric forms exhibit antifungal and insecticidal activity and can be used as agricultural and horticultural compounds for the protection of plants against fungi or insects.

Another aspect of the invention relates to fungicidal and insecticidal compositions comprising a novel compound of the invention in combination with suitable excipients, such as diluents, carriers, etc. due to the antifungal and insecticidal activity exhibited by the compounds of this invention.

Furthermore, the invention relates to methods of controlling plant diseases, especially originating from fungal or insecticidal attack, by application of compositions comprising the novel compounds of the invention to infested areas.

Within the context of the invention, it is also contemplated to combine the novel compounds of the invention with other pesticides or plant growth regulators for making up novel combination compositions.

The present invention therefore also embraces fungicidal compositions containing a compound of formula I, II, III, IV, V or VI as an active component. The invention contemplates the use of any of the compounds of the invention used alone or in combination with any other of the compounds of the invention or any other pesticide or plant growth regulator as active components in any fungicidal composition.

This invention also provides for insecticidal and fungicidal compositions comprising an insecticidal and fungicidal active compound according to the present invention and an agriculturally and horticulturally acceptable carrier material.

This invention further provides for a method of protecting plants from damage caused by fungus and/or insects comprising applying an effective amount of a fungicidal and insecticidal active compound of the present invention to said plant, e.g., by foliar application, or to the soil surrounding said plant.

This invention additionally provides for a method of protecting plant seeds from damage caused by fungus and/or insects comprising applying an effective amount of a fungicidal and insecticidal active compound of the present invention to said plant seeds.

This invention also provides for a method for controlling plant pathogenic fungi and insects comprising contacting said fungi or insects with an effective amount of a fungicidal and insecticidal active compound of the present invention.

DETAILED DESCRIPTION OF THE INVENTION

The present invention provides for a substantially pure strain of *Pyrenophora teres* belonging to the class Ascomycetes, designated CL806 (IMI CC# 351438), and a substantially pure fungal strain belonging to the class Deuteromycetes, designated 33-971 (IMI CC# 355496), and mutants thereof. The invention provides for the use of these microorganisms to produce the compounds of the invention as fungicidal and/or insecticidal compositions.

The invention provides for compounds of formulas I and IV and any tautomers thereof:

I

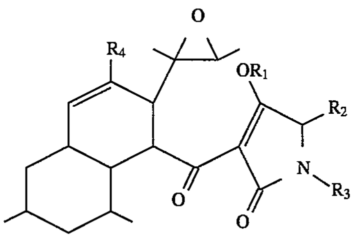

-continued

IV

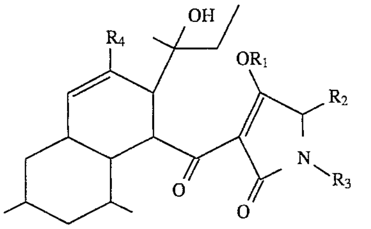

wherein $R_1$ is hydrogen, methyl or acetyl, or $R_1$ is sodium, potassium, lithium or any other salt;

$R_2$ is hydrogen or straight or branched $C_{1-10}$-alkyl;

$R_3$ is hydrogen or straight or branched $C_{1-10}$-alkyl; and $R_4$ is hydrogen or methyl.

Preferred compounds according to the present invention are the compounds of formulas II, III, V and VI shown above.

The compounds of formula II and III are obtainable as products from microorganisms belonging to the genus Pyrenophora and specifically *Pyrenophora teres* designated CL806 (IMI CC# 351438). These compounds may also be isolated from a species of Phoma. The compounds of formula V and VI are obtainable as products from fungi and specifically the fungal strain designated 33-971 (IMI CC# 355496).

The compounds of formulas I and IV include derivatives of the compounds of formulas II, III, V and VI. The derivatives can be synthesized from the compounds of formulas II, III, V and VI by methods well known to persons skilled in the art.

Another method for producing the compounds of formulas I, II, III, IV, V and VI is by traditional chemical synthesis from appropriate starting materials. In addition, the compound of formula II can be prepared by adding a salt solution such as sodium carbonate to the compound of formula III. The compound of formula III can be prepared by acidifying the compound of formula II. The epoxide group of the compounds of formula I may be opened to give the corresponding alcohol group in formula IV.

The fungicidal and insecticidal active compounds of formulas I, II, III, IV, V and VI, if derived preferably from a culture of Pyrenophora or other suitable fungal strain, may be purified so as to be essentially free of other fungal materials. The microbial production and purification of these compounds is described in the following sections.

Taxonomy and morphology of the organisms IMI CC# 351438

The fungus was identified as *Pyrenophora teres* Drechsler the perfect state of *Drechslera teres* (Sacc.) Shoemaker syn. *Helminthosphorium teres* Sacc. at the Plant Protection Centre, Lottenborgvej DK-2880 Lyngby, Denmark. This strain, which belongs to the class Ascomycetes and the order Pleosporales, was designated CL806 (International Mycological Institute CC# 351438) and was deposited according to the Budapest Treaty on Jan. 27, 1992.

The isolate was identified at the isolation time based on the characteristic symptoms on plants leaves (causes net blotch on barley). The identity was verified by microscopic examination of the culture and by reinoculation experiments on plants.

The conidiophores are solitary or in groups of 2–3, straight or flexuous often swollen at the base, pale to mid brown up to 200μμ long, 7–11μ thick, Conidia straight, cylindrical, rounded at the ends, subhyaline, smooth, and 1–10μ pseudoseptate, frequently with constriction, 79–160μ×16–23μ.

IMI CC# 355496

This fungal strain was isolated from plant material collected in the tropics. This strain, which belongs to the class Deteromycetes, was designated 33-971 (International Mycological Institute CC# 355496) and was deposited according to the Budapest Treaty on Jan. 6, 1993.

Production of the Compound of Formula II by Culturing

A slant culture of the isolate grown on PDA agar for 7 days at room temperature was mixed with 10 ml of sterile distilled water containing 0.1% Tween 80 and inoculated into 500 ml Erlenmeyer flasks containing 100 ml Yeast-Extract-Sucrose medium using tap water (2% yeast extract (Difco); 15% sucrose; 10 ppm $ZnSO_4.7H_2O$, 5 ppm $CuSO_4.5H_2O$ and 3 g wheat bran). The pB was adjusted to 6.4 before the substrate was autoclaved at 121° C. for 40 minutes. After inoculation, the flask was placed at 26° C. and shaken at 120 rpm for 14 days.

While it is preferred that the fungus be grown as described above in order to express the active compound, it can also be expressed by growing the fungus in the following fermentation media:

Yeast-Extract-Sucrose medium using distilled water:
2% yeast extract (Difco); 15% sucrose; 10 ppm $ZnSO_4.7H_2O$, 5 ppm $CuSO_4.5H_2O$. The pH was adjusted to 6.4 before the substrate was sterilized at 121° C. for 40 minutes.

Yeast-Extract-Sucrose medium using distilled water:
2% yeast extract (Difco); 15% sucrose; 0.05% $MgSO_4.7H_2O$; 10 ppm $ZnSO_4.7H_2O$, 5 ppm $CuSO_4.5H_2O$. The pH was adjusted to 6.4 before the substrate was autoclaved at 121° C. for 40 minutes.

Yeast-Extract-Glucose medium using distilled water;
0.4% yeast extract; 0.1% $KH_2PO_4$, 0.05% $MgSO_4.7H_2O$; glucose 1.5%; pluronic 0.1 ml/L. pH 5.4 after autoclaving at 121° C. for 20 minutes.

Fries-saccharose medium:
0.1% $KH_2PO_4$; 0.05% $MgSO_4.7H_2O$; NaCl 0.01%, 0.013% $CaCl_2.2H_2O$, 0.1% $NH_4NO_3$; 0.5% $(NH_4NO_3)$tartrate, 3% saccharose, 1 ml/L of the following stock culture (1 L): 1.0 mg $MnSO_4.4H_2O$, 1.0 mg Boron acid; 0.1 mg $CuSO_4$, 0.1 mg $ZnSO_4$, 20 mg $FeSO_4.7H_2O$. The pH was adjusted to 6.5 before the substrate was autoclaved at 121° C. for 40 minutes.

Extraction of the Compound of Formula II

The fungicidal and insecticidal active compound was extracted from the culture broth as follows:

100 ml hexane was added to the broth from one, flask and shaken at 18° C. for 2 hrs and then placed at 4° C. for 16 hours. The hexane supernatant containing the metabolite was separated from the broth including mycelium after a centrifugation for 10 min. at 20,000 rpm.

Purification of the Compound of Formula II

The crude extract obtained above was purified by flash chromatography on silica gel 60. The crude extract was loaded onto the column and a gradient of solvents from hexane to ethyl acetate to methanol was applied. The active compound was eluted with 10:90 methanol:ethyl acetate. The details of the HPLC method are set forth below in Table 1.

TABLE 1

| Analysis - HPLC method | |
|---|---|
| Column: | Brownlee ODS C-18, 4.6 mm × 250 mm |
| Flow: | 2 mL/minute |
| Eluent: | Acetonitrile + 0.05% TFA (trifluoroacetic acid). |
| Detector: | UV, 254 nm |
| Retention time: | ~3 minutes |

Chemical Characteristics of the Compounds of Formulas II and III

The Compound of Formula II

The substantially pure fungicidal and insecticidal active compound of formula II has the following physical characteristics:

Molecular formula: $C_{26}H_{38}NO_4Na$ from high resolution mass spec, the molecular ion ($M^+$+$H^+$–$Na^+$) is found to be 430.2585 (430.2947 calculated) UV spectral data (ethanol): UV 244 nm (ε=5694), 291 nm (ε=8001). IR: (NaCl) Vmax: 1475, 1610, 2950 (br) $cm^{-1}$.

NMR data for the compound of formula II is set forth below: $^1$H NMR ($CDCl_3$) δ0.8(m, 6H), 0.9(m, 6H), 1.2(m, 8H), 1.7(3H), 1.9 (m, 1H), 2.3(m, 2H), 2.7(m, 3H), 3.4(m, 1H), 3.7(q, 1H), 4.6(m, 1H), 5.2(m, 1H), 5.7(m, 1H).

$^{13}$C NMR ($CDCl_3$) δ12.0(q), 12.5(q), 13.3(q), 13.9(q), 22.4(q,2x), 24.7(t), 26.4(q), 33.7(d), 36.2(d), 37.9(d,2x), 38.1(t), 38.4(d), 38.5(t), 40.3(d), 52.8(d), 59.7(d), 66.4(s), 68.8(d), 104.1(s), 125.4(d), 133.8(d), 175.5(s), 193.2(s), 198.5(s).

The compound of formula II is soluble in hexane, chloroform, ethyl acetate and sparingly soluble in methanol. The compound of formula II can be prepared by adding a salt solution such as sodium carbonate to the compound of formula III.

The Compound of Formula III

The substantially pure fungicidal and insecticidal active compound of formula III is an amorphous solid which has the following physical characteristics:

Molecular formula: $C_{26}H_{39}NO_4$ from high resolution mass spec, the molecular ion ($M^+$+$H^+$) was found to be 430.2585 (430.2947 calculated). UV spectral data (ethanol): UV 244 nm (ε=5694), 291 nm (ε=8001). IR: (NaCl) Vmax: 1475, 1610, 2950 (br) $cm^{-1}$.

The NMR data for the compound of formula III is set forth below: $^1$H NMR ($CDCl_3$) δ0.83 (d, 3H), 0.90 (d, 3H), 0.98(d, 3H), 0.98(t, 3H), 1.05(m, 2H), 1.18(s, 3H), 1.20(m, 1H), 1.25(d, 3H), 1.50(m, 2H), 1.70(m, 3H), 1.95(m, 1H), 2.09(m, 1H), 2.21(m, 1H), 2.40(m, 1H), 2.83(q, 1H), 2.94(s, 3H), 3.68 (d, 1H), 4.24(dd, 1H, J=9.1, 9.0 Hz), 5.34(m, 1H), 5.80(m, 1H).

$^{13}$C NMR ($CDCl_3$) δ12.2(q), 12.4(q), 14.0(q), 14.1(q), 20.4(q), 22.3(q), 25.2(t), 26.7(q), 33.3(d), 35.2(d), 35.8(d), 37.8(t), 37.90(t), 37.95(d) 40.0(d), 41.9(d), 51.5(d), 58.7(d), 63.0(s), 69.9(d), 103.9(s), 125.2(d), 133.8(d), 173.6(s), 190.3(s), 193.9(s).

The compound of formula III is soluble in hexane, chloroform, ethyl acetate and sparingly soluble in methanol. The compound of formula III can be prepared by acidifying the compound of formula II.

Production of the Compounds of Formulas V and VI by Culturing

A slant culture of the isolate grown on YPG-1 agar (Yeast extract 4 g/L, Glucose 15 g/L, $KH_2PO_4$, 1 g/L, $MgSO_4.7H_2O$ 0.5 g/L and Bacto agar 15 g/L) for 14 days at 26° C. was mixed with 10 ml of sterile distilled water containing 0.1% Tween 80 and inoculated into 500 ml Erlenmeyer flasks containing 45 ml (YPG-1 bouillon using tap water and 30 g wheat bran). The medium was autoclaved at 121° C. for 45 minutes.

After inoculation, the flasks were placed at 26° C. for 15 days.

Extraction of the Compounds of Formulas V and VI

The compounds were extracted from the flasks as follows: 200 ml ethanol was added to one flask and shaken at 18° C. overnight. The ethanol supernatant containing the metabolites was separated from the growth medium including mycelium by centrifugation for 10 min at 20,000 rpm. The sediment containing the mycelium and wheat bran was discarded and the supernatant was analyzed for activity.

Purification of the Compounds of Formulas V and VI

The crude extract obtained above was purified by flash chromatography on silica gel 60. The crude extract was loaded onto the column and a gradient of solvents from hexane to ethyl acetate to methanol was applied. The active compound was eluted with 10:90 methanol:ethyl acetate. The details of the HPLC method are set forth below in Table 1.

Chemical characteristics of the Compounds of Formulas V and VI

The Compound of Formula V

The substantially pure fungicidal and insecticidal active compound of formula V has the following physical characteristics:

The molecular ion $(M+H)^+$ was found to be 430 specifying a molecular formula of $C_{26}H_{39}NO_4$.

UV spectral data (methanol): UV 225 nm (ε=12312), 292 nm (ε=15489).

NMR data for the compound of formula V is set forth below: $^1$H NMR ($CDCl_3$): 0.89(d, 3H, J=7.5 Hz), 0.92(d, 3H, J=7.1 Hz), 0.97 (d, 3H, J=6.4 Hz), 1.04(m, 1H), 1.06(m, 1H), 1.13(d, 3H, J=7.1 Hz), 1.15(s, 3H), 1.24 (d, 3H, J=5.6 Hz), 1.25(m, 1H), 1.46(m, 1H), 1.59(br d, 3H, J=1.5 Hz), 1.67(m, 1H), 1.72(m, 1H), 2.03(m, 1H), 2.15(dt, 1H, J=11, J=3.6 Hz), 2.28(d septet, 1H, J=7, J=3.1 Hz), 2.29(br d, 1H, J=10 Hz), 2.28(d septet, 1H, J=7, J=3.1 Hz), 2.29 (br d, 1H, J=10 Hz), 2.83(q, 1H, J=5.5 Hz), 2.97(s, 3H), 3.61(d, 1H, J=3.1 Hz), 4.37(dd, 1H, J=11, J=10 Hz), 5.60(d pentet, 1H, J=5.8, J=1.5 Hz).

$^{15}$C NMR ($CDCl_3$): 11.7(q), 13.6(q), 17.2(q), 17.4(q), 20.3(q), 21.4(q), 22.3(q), 27.2(q), 29.2(d), 33.2(d), 35.5(d), 37.7(t,2x), 37.9(d), 40.2(d), 41.9(d), 54.0(d), 60.5(d), 62.2(s), 71.1(d), 103.9(s), 130.6(s), 130.6(d), 173.8(s), 190.9(s), 194.0(s),

The compound of formula V is soluble in chloroform, ethyl acetate, methanol, hexane and heptane.

The Compound of Formula VI

The substantially pure fungicidal and insecticidal active compound of formula VI has the following physical characteristics:

The molecular ion $(M+H)^+$ was found to be 444 specifying a molecular formula of $C_{27}H_{41}NO_4$.

UV spectral data (methanol): UV 222 nm (ε=18211), 291 nm (ε=16671).

NMR data for the compound of formula VI is set forth below: $^1$H NMR ($CDCl_3$): 0.84(d, 3H, J=7.0 Hz), 0.90(d, 3H, J=7.4 Hz), 0.97(d, 3H, J=6.2 Hz), 0.98(d, 3H, J=7.2 Hz), 1.03(m, 1H), 1.07(m, 1H), 1.14(s, 1H), 1.23 (m, 1H), 1.23(s, 3H), 1.43(m, 1H), 1.56(m, 1H), 1.59(s, 3H), 1.66(m, 1H), 1.68(m, 1H), 1.72(m, 1H), 1.96(m, 1H), 2.03(m, 1H), 2.14(dt, 1H, J=11, J=3.0 Hz), 2.28(br d, 1H, J=10 Hz), 2.82(q, 1H, J=5.4 Hz), 2.94(s, 3H), 3.70(d, 1H, J=3.0 Hz), 4.35(t, 1H, J=10 Hz), 5.60(br d, 1H, J=5 Hz).

$^{15}$C NMR ($CDCl_3$): 11.7(q), 12.4(q), 13.6(q), 14.1(q), 20.3(q), 21.4(q), 22.3(q), 25.2(t), 26.7(q), 33.2(d), 35.6(d), 35.8(d), 37.7(t,2x), 37.9(d), 40.2(d), 41.9(d), 54.0(d), 60.6(d), 62.3(d), 69.9(d), 104.1(s), 130.6(s), 130.8(d), 173.7(s), 190.8(s), 194.1(s).

The compound of formula VI is soluble in chloroform, ethyl acetate, methanol, hexane and heptane.

Formulations of the Active Compounds

A fungicidal composition according to the invention comprising a fungicidally active compound of the invention as its active ingredient may for agronomical and/or horticultural applications be formulated by mixing the active compound with suitable inert and compatible carriers or diluents to obtain a composition of the type generally used in agricultural compositions such as a wettable powder, an emulsifiable concentrate, a concentrated emulsion, a granular formulation, a water soluble powder, solutions, suspension, concentrates, release formulations (including slow release formulations), an alginate, a xanthan gum, solutions and/or an aerosol. As solid carriers bentonite diatomaceous earth, apatite, gypsum, talc, pyrophyllite, vermiculite, ground shells, and clay may be mentioned. A surface active agent may also be added with the purpose of producing a homogeneous and stable formulation.

The diluent or carrier in the composition of the invention can as indicated be a solid or a liquid optionally in association with a surface-active agent, for example a dispersing agent, emulsifying agent or wetting agent. Suitable surface-active agents include anionic compounds such as a carboxylate, for example a metal carboxylate of a long chain fatty acid; an N-acylsarcosinate; mono- or di-esters of phosphoric acid with fatty alcohol ethoxylates or salts of such esters; fatty alcohol sulphates such as sodium dodecyl sulphate, sodium octadecyl sulphate or sodium cetyl sulphate; ethoxylated fatty alcohol sulphates; ethoxylated alkylphenol sulphates; lignin sulphonates; petroleum sulphonates; alkyl aryl sulphonates such as alkyl-benzene sulphonates or lower alkylnaphthalene sulphonates, e.g. butylnaphthalene sulphonate; salts or sulphonated naphthalene-formaldehyde condensates; salts of sulphonated phenol-formaldehyde condensates; or more complex sulphonates such as the amide sulphonates, e.g., the sulphonated condensation product of oleic acid and N-methyl taurine or the dialkyl sulphosuccinates, e.g. the sodium sulphonate or dioctyl succinate. Non-ionic agents include condensation products of fatty acid esters, fatty alcohols, fatty acid amides or fatty-alkyl- of alkenyl-substituted phenols with ethylene oxide, fatty esters of polyhydric alcohol ethers, e.g. sorbitan fatty acid esters, condensation products of such esters with ethylene oxide, e.g. polyoxyethylene sorbitan fatty acid esters, block copolymers of ethylene oxide and propylene oxide, acetylenic glycols such as 2,4,7,9-tetraethyl-5-decyn-4,7-diol, or ethoxylated acetylenic glycols.

Examples of a cationic surface-active agent include, for instance, an aliphatic mono-, di-, or polyamine as an acetate, naphthenate or oleate; an oxygen-containing amine such as an amine oxide of polyoxyethylene alkylamine; an amide-linked amine prepared by the condensation of a carboxylic acid with a di- or polyamine; or a quaternary ammonium salt.

The compositions of the invention can take any form known in the art for the formulation of agrochemicals, for example, a solution, a dispersion, an aqueous emulsion, a dusting powder, a seed dressing, a dispersible powder, an emulsifiable concentrate or granules. Moreover, it can be with a suitable form for direct application or as a concentrate or primary composition which required dilution with a suitable quantity of water or other diluent before application.

An emulsifiable concentrate comprises the active ingredient dissolved in a water-immiscible solvent which is formed into an emulsion with water in the presence of an emulsifying agent.

A dusting powder comprises the active ingredient intimately mixed and ground with a solid pulverulent diluent, for example, kaolin.

A granular solid comprises the active ingredient associated with similar diluents to those which may be employed in dusting powders, but the mixture is granulated by known methods. Alternatively it comprises the active ingredient absorbed or adsorbed on a pre-granular diluent for example, Fuller's earth, attapulgite or limestone grit.

Wettable powders, granules or grains usually comprise the active ingredient in admixture with a suitable surfactant and an inert powder diluent such as china clay.

Another suitable concentrate is a flowable suspension concentrate which is formed by grinding the active ingredient with water or other liquid, a wetting agent and suspending agent.

The concentration of the active compound of the invention described herein in the compositions of the invention may vary within a wide range depending on the type of formulation and the field of application.

It is contemplated that the active compound of the invention may be applied in concentrations ranging from about 0.01 mg/ml to 10 mg/ml, preferably from 0.1 mg/ml to 2 mg/ml, for use in controlling fungi in plants.

Depending on the circumstances such as the crop wherein fungi are to be combated, the environmental conditions or other factors, a composition of the invention in addition to said fungicidally active compounds of the invention may also contain other active ingredients such as other pesticides, fungicides, herbicides, insecticides, nematicides, acaricides or plant nutrients, growth regulators or fertilizers.

Examples of other fungicides which can be combined with the active compounds of the invention include ergosterol biosynthesis inhibitors ("EBIs"). These are generally imidazole or triazole derivatives and examples include those known by the common names prochloraz, triadimefon, propiconazole, diclobutrazol, triadiminol, flusilazole, flutriafol, myclobutanil, penconazole, quinconazole, imazalil and diniconazole. Examples of non azole EBIs include naurimol, fenarimol, fenpropimorph, tridemorph and fenpropidine. Other fungicides which can be combined with the enzyme preparation of the invention include:

- Dithiocarbamates, e.g. thiram, maneb, zineb and mancozeb;
- Phatalimides, e.g. captan, folpet and captafol;
- Carboxines, e.g. carboxin and oxycarboxin;
- Benzimidazoles, e.g. benomyl, carbendazim and fuberidazole;
- Carbamates, e.g. prothiocarb and propamocarb;
- Isoxazoles, e.g. hymexazol;
- Cyanoacetamides, e.g. cymoxanil;
- Ethylphosphonates, e.g. fosetylaluminium;
- Phenylamides, e.g. furalaxyl, metalaxyl, benalaxyl, ofurace, cyprofuram and oxandixyl;
- Dicarboximides, e.g. procymidone, iprodione and vinclozolin;
- Organophosphorous fungirides, e.g. pyrazophos, triamiphos, ditalimfos and tolcofosmethyl; and
- Aromatic hydrocarbon fungicides, e.g. quintozene, dichloren and diphenyl.

Another aspect of the invention relates to methods of controlling fungi in plants, wherein an effective amount of a fungicidally active compound of the invention is applied to a region to be treated. In connection with this aspect of the invention the compositions may be applied to a region to be treated either directly to the soil as a pre-emergence treatment or to the foliage or fruits of the plants as a post-emergence treatment. Depending on the crop and circumstances the treatment may be postponed until seeds or fruits appear on the plants, wherein fungi are to be controlled.

The active preparation or the compositions of the invention can be applied directly to the plant by, for example, spraying or dusting either at the time when the pests have begun to appear on the plant or before the appearance of pests as a protective measure. In both such cases the preferred mode of application is by foliar spraying. It is generally important to obtain good control of pests in the early stages of plant growth as this is the time when the plant can be most severely damaged. The spray or dust can conveniently contain another pesticide or a pre- or post-emergence herbicide if this is thought necessary.

Sometimes, it is practicable to treat the roots of a plant before or during planting, for example by dipping the roots in a suitable liquid or solid composition. When the active preparation of the invention is applied directly to the plant a suitable rate of application is from 5 g to 5 kg per hectare, preferably from 100 g to 2 kg per hectare.

In the method of the invention the active preparation of the invention alone or in combination with a conventional pesticide can also be applied to seeds or habitat. Thus the preparation can be applied directly to the soil before, at or after drilling so that the presence of active ingredient in the soil can control the growth of fungi which may attack seeds.

The compositions of this invention, including the compound of formula I, II, III, IV, V or VI, may be applied in amounts corresponding to from about 5 g to about 5 kg active compound per hectare. When the soil is treated directly the active preparation alone or in admixture with the conventional pesticide can be applied in any manner which allows it to be intimately mixed with the soil such as by spraying, by broadcasting a solid form of granules, or by applying the active ingredient at the same time as drilling by inserting it in the same drill as the seeds. A suitable application rate is within the range of from 5 g to 5 kg per hectare, more preferably from 100 g to 2 kg per hectare.

The concentration of the fungicidally active compounds of the invention in the compositions of the present invention when used alone or in combination with a conventional fungicide, as applied to plants is preferably within the range from about 0.001 to about 30 percent by weight, especially 0.01 to 3.0 percent by weight. In a primary composition the amount of active compound can vary widely and can be, for example, in the range from about 5 to about 95 percent by weight of the composition.

The concentration of the other fungicidally active ingredient in the mixed composition of the present invention, as applied to plants is preferably within the range of 0.001 to 50 percent by weight, especially 0.01 to 10 percent by weight. In a primary composition the amount of other active ingredient can vary widely and can be, for example, from 5 to 80 percent by weight of the composition.

Although the present invention has been described in detail in connection with controlling fungi or insects, it is also anticipated that the active compounds of the invention may be used for controlling fungi in the preservation of wood by adding said compounds to wood preservation and/or impregnation compositions. Also, the active compounds of the invention may be useful as a fungicide and preservative in paints—both to prevent growth in the paint during storage, and growth on the painted object such as the plastered surface of a house.

EXAMPLES

EXAMPLE 1

Fungicidal activity of the Compound of Formula II

The compound of formula II has been shown to have an inhibitory effect on the growth of fungi belonging to the classes Oomycetes, Ascomycetes, and Deuteromycetes. It was found to be particularly potent towards:

Class Oomycetes
- Pythium sp. Type F.
- *Phytophthora infertans*
- *Plasmonpara viticola*

Class Ascomycetes
- *Pyrenophora teres*
- *Phoma betae*
- *Phoma lingam*
- *Ascochyta pisi*
- *Venturia inaqualis*
- *Saccharomyces cerevisiae*

Class Deuteromycetes
- *Fusarium oxysporum*
- *Botrytis cinerea*
- *Rhizoctonia solani* (AG-3)
- *Monilinia fructigena*
- *Aspergillus niger*

In vitro assay

The compound of formula II has been found to have an in vitro inhibitory effect on the growth of fungi (Table 2). In the in vitro assay the test organisms were embedded in agar media. Small wells were punched in the agar and 15 μl sample of each concentration was applied to the wells. Clearing zones indicating inhibition of the test organism were measured after two days incubation at room temperature. In vitro results after screening of different concentrations of the compound for activity against 5 Ascomycetes and 1 Deuteromycetes (*Monilinia fructigena*) are shown in Table 2. The inhibition is expressed as mm clearing zones (−1 indicates that the inhibition zone is unclear).

TABLE 2

| | mg a.i./ml | |
|---|---|---|
| Test strain | 1.0 | 0.1 |
| *Pyrenophora teres* | 33-1 | 18-1 |
| *Phoma betae* | 13-1 | — |
| *Phoma lingam* | 9 | — |
| *Ascochyta pisi* | 13 | — |
| *Venturia inaequalis* | 13 | 8-1 |
| *Monilinia fructigena* | 12 | 8 |

The inhibitory activity against Pythium and *Phytophthora infestans* was estimated using a microtiter assay: 1 ml of a liquid media was applied to each well in a 24 well microtiter plate (Media 1 for the Pythium assay and Media 2 for the Phytophthora assay). 20 μl sample of each concentration was then applied to each well followed by 100 μl sporangia suspension (for the *P. infestans*) or 100 μl of a zoospore suspension (for the Pythium assay).

Media 1: 0.9 ml diluted salt solution (Dill, B. C. & M. S. Fuller (1971) *Archiv. Microb.*, Vol. 87, pp. 92–98) and 0.1 ml Yeast Peptone glucose broth were mixed before application to each well.

Media 2: 0.9 ml diluted salt solution and 0.1 ml Pea suspension were mixed before application to each well.

Microtiter plates with *P. infestans* were incubated in diffuse light at 17°–20° C. After 3 days fungal growth was estimated.

Microtiter plates with Pythium were incubated at 30° C. After 1 day the fungal growth was estimated.

In vitro results after screening of different concentrations of the compound for activity against 2 Oomycetes using the previously described microtiter assay are shown in Table 3. The character 4 indicates total inhibition of fungal growth.

TABLE 3

| | mg a.i./ml | | | |
|---|---|---|---|---|
| Test strain | 2.0 | 0.4 | 0.3 | 0.25 |
| Pythium sp. | 4 | 4 | 4 | 4 |
| *Phytophthora infestans* | 4 | 4 | 4 | — |

EXAMPLE 2

Activity of the compound of formula II against *Phytophthora infestans* Host: *Solanum tuberosum* (Potato, var. Sava)

Potato plants (3–4 weeks old) were sprayed to run off with liquid suspensions using a handhold sprayer (Bink Bullows 900). The suspensions (MeOH 50%) contained respectively 750 ppm, 500 ppm, 250 ppm and 125 ppm of formula II. Four replicates were used at each concentration. The plants were kept 24 hours in a green house to dry before they were inoculated with a suspension of sporangia spores containing $1\times10^5$ spores per ml. The inoculation was carried out with a handheld atomizer (Wagner, Pico Bel). The plants were then incubated in clear polythene bags, which stayed on for the whole test period, to raise the relative humidity to 95–100%. For the first 24 hours the plants were not exposed to any light and the temperature was kept at 18° C. Thereafter the conditions were: 16 hours light (app. 10,000 lux) and 8 hours dark. The temperature was in the daylight period 18° C. and during night 13° C.

After 6 days the assessment was done. The results are shown in Table 4:

TABLE 4

| |
|---|
| 750 ppm: approx. 90% protection |
| 500 ppm: approx. 75% protection |
| 250 ppm: approx. 50% protection |
| 125 ppm: approx. 30% protection |

EXAMPLE 3

Activity of the compound of formula II against *Plasmopara viticola* Host: *Vitis vinifera* (vine, var. Ugni Blano)

Vine plants (5–6 weeks old) were sprayed to run off with a liquid suspension using a handheld sprayer (Bink Bullows 900). The suspensions (MeOH 50%) contained respectively 750 ppm, 500 ppm, 250 ppm and 125 ppm of formula II. Four replicates were used at each concentration. The plants were kept 24 hours in a green house to dry before they were inoculated with a spore suspension containing $1\times10^5$ spores per ml. The inoculation was carried out with a handheld atomizer (Wagner, Pico Bel). The plants were then incubated (16 hours light (app. 10,000 Lux) and 8 hours darkness) at 20° C. in clear polythene bags, which stayed on for the whole test period, to raise the relative humidity to 95–100%.

After 6 days the assessment was done. The results are shown in Table 5:

TABLE 5

| |
|---|
| 750 ppm: approx. 100% protection |
| 500 ppm: approx. 100% protection |
| 250 ppm: approx. 90% protection |
| 125 ppm: approx. 90% protection |

Insecticidal activity of the compound of formula II

The compound of formula II has also been shown to have an inhibitory effect on the growth of insects belonging to the following genera:

*Spodoptera exigua*

*Helicoverpa virescens*

*Drosophila melanogaster*

*Trichoplusia ni.*

It is also expected that this compound will be active against other similar and/or related insects.

Description of Insect Bioassays

*Spodoptera exigua* and *Helicoverpa virescens:*

Larval diet was mixed with test compound (which has been evaporated on alpha-cellulose) to the desired concentration. The diet (1 ml) was poured into each of 10 wells in a well tray. Eggs of the insect were suspended in agar at 1.2 g/L (3–6 eggs/50 µl). Three to six eggs in an agar suspension were added to each well. Trays were covered with mylar and each well is perforated with air holes. Test trays were incubated at 28° C. Mortality and stunting were determined after 7 days.

*Drosophila melanogaster:*

The diet was prepared as described above and 13×100 test tubes are filled with 2 ml of treated diet. Tubes were infested with 8–10 one week old adult *D. melanogaster.* Tubes were incubated and scored as described above. The results of these assays are shown in Table 6.

TABLE 6

| Active ingredient: | 1000 ppm | 100 ppm | 10 ppm |
|---|---|---|---|
| *Spodoptera exigua* | 0.9 | 1.3 | 3.0 |
| *Helicoverpa virescens* | 0.6 | 1.5 | 2.6 |
| *Drosophila melanogaster* | 0.0 | 3.5 | 4.0 |

[the numbers indicate a stunting effect with 0 being the most severe stunt (no growth) and 4 being control or no effect]

*Trichoplusia ni:*

4 g larvae diet was poured into each of 25 cups made in form pressured transparent plastic in a tray. The diet stood for 2 hours for evaporation and cooling. 100 µl of test ingredient, methanol (control) or water (control) was applied topically on the diet with a micropipette. All applications were duplicated. The tray was tilted and turned to secure that the fluid totally covered the surface in each cup. The tray was covered with paper for 16 hours.

Five second instar larvae were put into each cup and the trays were then covered with a transparent plastic folio which was ironed on and then pierced to avoid condensation of water in the cups. The trays were placed in temperature and light regulated chambers (30° C.), 16/8 light on/off) for 4 days. Results (% mortality) were read after 1 day and four days and are shown in Table 7.

TABLE 7

| Active Ingredient: | 2000 ppm | 400 ppm | 250 ppm |
|---|---|---|---|
| *Trichoplusia ni* | 4 | 4 | 4 |

TABLE 7-continued

| Active Ingredient: | 2000 ppm | 400 ppm | 250 ppm |
|---|---|---|---|

[numbers indicate a stunting effect with a scale of 0–4, where 0 is no effect and 4 is the strongest effect]

Per oral tox test

This example was made on the crude hexane extract using corn oil as the "solvent" introduced as a per oral test with 3 different concentrations of the extract of the compound of formula II: 18 mg/kg (mouse), 400 mg/kg and 917 mg/kg as a modification of the method described in the OECD's guidelines. None of these concentrations of the compound of formula II showed any toxicity against the mice.

EXAMPLE 4

Fungicidal activity of the Compounds of Formulas V and VI

An ethanol extract of the broth containing the compounds of formulas V and VI had an inhibitory effect on the growth of fungi belonging to the classes Deuteromycetes and Oomycetes.

Using the in vitro assay described at page 19, lines 10–20, the extract also had an in vitro inhibitory effect on the growth of *Botrytis cinerea* belonging to the Class Deuteromycetes.

The extract inhibited *Botrytis cinerea* expressed as a 20 mm unclear inhibition zone and had an in vitro inhibition effect on the growth of both gram positive and gram negative bacteria—gram positive: *Bacillus subtilis* and gram negative: Pseudomonas.

The extract also had an in vivo inhibition against the class Oomycetes, e.g., *Phytophthora infestens.*

The extract also had an inhibitory effect on the growth of *Trichoplusia ni* using the insect bioassay described in Example 3 (page 24, lines 1–12).

Activity of the Compound of Formula V against *Phytophthora infestans* Host: *Solanum tuberosum* (Potato, var Sava)

Potato plants (3–4 weeks old) were sprayed to run off with liquid suspensions using a handheld sprayer (Bink Bullows 900). The suspensions (MeOH 70%) contained respectively 1000 ppm, 100 ppm and 10 ppm of the compound. Four replicates were used at each concentration. The plants were kept 24 hours in a green house to dry before they were inoculated with a suspension of *Phytophthora infestans* sporangia spores containing $1\times10^5$ spores per ml. The inoculation was carried out with a handheld atomizer (Wagner, Pico Bel). The plants were then incubated in clear polythene bags, which stayed on for the whole test period, to raise the relative humidity to 95–100%. For the first 24 hours, the plants were not exposed to any light and the temperature was kept at 18° C. Thereafter the conditions were 16 hours light (app. 10,000 lux) and 8 hours dark. The temperature during the daylight period was 18° C. and during night 13° C.

After 6 days, the assessment was done. The results are shown in the Table 8:

TABLE 8

| | | |
|---|---|---|
| 1000 ppm: approx. | 100% protection (9p1) |
| 100 ppm: approx. | 55% protection (5p1) |
| 10 ppm: approx. | 30% protection (3p0) |

Activity of the Compound of Formula V against *Bacillus subtilis, Saccharomyces cerevisiae, Aspergillus niger, Fusarium oxysporum, Botrytis cinerea* and *Rhizoctonia solani.*

The compound of formula V was found to have an in vitro inhibitory effect on the growth of the above fungi at three concentrations, i.e., 1000 ppm, 100 ppm and 10 ppm, using the in vitro assay described at page 19, lines 10–20. The results are provided in Table 9.

TABLE 9

| ppp | *B. sub.* | *P. Aer.* | *S. cer.* | *A. nig.* | *F. oxy.* | *B. cin.* | *R. sol.* |
|---|---|---|---|---|---|---|---|
| 1000 | 10-0 | 0 | 11-0 | 8-1 | 8-1 | 12-1 | 7-1 |
| 100 | 10-0 | 0 | 10-0 | 6-1 | 0 | 11-1 | 7-1 |
| 10 | 10-0 | 0 | 0 | 0 | 0 | 0 | 0 |

The compound of formula V was also found to have an inhibitory effect on the growth of *Trichoplusia ni* using the procedure described at page 24, lines 1–12. The results are shown in Table 10.

TABLE 10

| Active Ingredient: | 1000 ppm | 100 ppm | 10 ppm |
|---|---|---|---|
| *Trichoplusia ni* | 2-1 | 0-0 | 0-0 |

[numbers indicate a stunting effect with a scale of 0–4, where 0 is no effect and 4 is the strongest effect]

The present invention is not to be limited in scope by the above examples since they are intended as single illustrations of the invention. Indeed, various modifications of the invention in addition to those shown and described herein will become apparent to those skilled in the art from the foregoing description. Such modifications are intended to fall within the scope of the appended claims.

We claim:

1. A substantially pure strain of *Pyrenophora teres* IMI CC no. 351438 or a mutant thereof.

2. A substantially pure strain of fungal strain IMI CC no. 355496 or a mutant thereof.

3. A compound of formula I or a tautomer thereof:

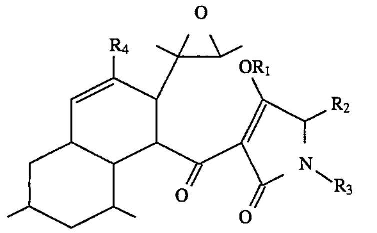

I wherein $R_1$ is hydrogen, methyl or acetyl, or $R_1$ is sodium, potassium, lithium or any other agriculturally-acceptable salt;

$R_2$ is hydrogen or straight or branched $C_{1-10}$-alkyl;

$R_3$ is hydrogen or straight or branched $C_{1-10}$-alkyl; and $R_4$ is hydrogen or methyl.

4. The compound according to claim 3, wherein $R_1$ is Na, $R_2$ is isobutyl, $R_3$ is methyl and $R_4$ is hydrogen.

5. The compound according to claim 3, wherein $R_1$ is hydrogen, $R_2$ is isobutyl, $R_3$ is methyl and $R_4$ is hydrogen.

6. The compound according to claim 3, wherein $R_1$ is hydrogen, $R_2$ is isobutyl, $R_3$ is methyl and $R_4$ is methyl.

7. The compound according to claim 3, wherein $R_1$ is hydrogen, $R_2$ is isopropyl, $R_3$ is methyl and $R_4$ is methyl.

8. A compound of formula IV or a tautomer thereof:

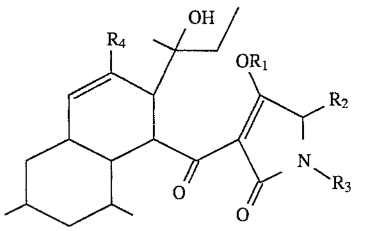

IV wherein $R_1$ is hydrogen, methyl or acetate, or $R_1$ is sodium, potassium, lithium or any other salt;

$R_2$ is hydrogen or straight or branched $C_{1-10}$-alkyl;

$R_3$ is hydrogen or straight or branched $C_{1-10}$-alkyl; and $R_4$ is hydrogen or methyl;

or a tautomer thereof.

9. The compound according to claim 8, wherein $R_1$ is Na, $R_2$ is isobutyl, $R_3$ is methyl and $R_4$ is hydrogen.

10. The compound according to claim 8, wherein $R_1$ is hydrogen, $R_2$ is isobutyl, $R_3$ is methyl and $R_4$ is hydrogen.

11. The compound according to claim 8, wherein $R_1$ is hydrogen, $R_2$ is isobutyl, $R_3$ is methyl and $R_4$ is methyl.

12. The compound according to claim 8, wherein $R_1$ is hydrogen, $R_2$ is isopropyl, $R_3$ is methyl and $R_4$ is methyl.

13. An insecticidal composition comprising the compound of claim 3 and an agriculturally acceptable excipient.

14. A fungicidal composition comprising the compound of claim 8 and an agriculturally acceptable excipient.

15. A method of protecting plants or plant seeds from damage caused by fungi or insects, comprising applying an effective amount of the compound of claim 3 and an agriculturally acceptable excipient to said plants, to the soil surrounding said plants or to said plant seeds.

16. The method according to claim 15, wherein the compound and the agriculturally acceptable excipient are applied by foliar application.

17. A method of protecting plants or plant seeds from damage caused by fungi or insects, comprising applying an effective amount of the compound of claim 8 and an agriculturally acceptable excipient to said plants, to the soil surrounding said plants or to said plant seeds.

18. The method according to claim 17, wherein the compound and the agriculturally acceptable excipient are applied by foliar application.

* * * * *